United States Patent
Mounfield, Jr. et al.

(10) Patent No.: US 10,766,624 B2
(45) Date of Patent: Sep. 8, 2020

(54) ALGORITHM FOR EFFICIENTLY BREAKING A MATERIAL

(71) Applicant: Honeywell International Inc., Morris Plains, NJ (US)

(72) Inventors: William Pratt Mounfield, Jr., Norcross, GA (US); Paul John Pappafotis, Snellville, GA (US)

(73) Assignee: Honeywell International Inc., Morristown, NJ (US)

( * ) Notice: Subject to any disclaimer, the term of this patent is extended or adjusted under 35 U.S.C. 154(b) by 638 days.

(21) Appl. No.: 15/153,511

(22) Filed: May 12, 2016

(65) Prior Publication Data

US 2017/0203846 A1  Jul. 20, 2017

Related U.S. Application Data

(60) Provisional application No. 62/281,157, filed on Jan. 20, 2016.

(51) Int. Cl.
    *B64D 15/16*      (2006.01)
    *B25D 17/00*      (2006.01)
    (Continued)

(52) U.S. Cl.
CPC ........ *B64D 15/16* (2013.01); *A61B 17/22004* (2013.01); *A61C 1/07* (2013.01);
(Continued)

(58) Field of Classification Search
CPC ..... B64D 15/16; A61B 17/22004; A61B 1/07; B25D 17/00; B25D 2222/15; A61C 1/0007; A61C 3/03
(Continued)

(56) References Cited

U.S. PATENT DOCUMENTS 4,368,471 A * 1/1983 Walton, Jr. ............... H01Q 1/02
    343/704
4,545,553 A * 10/1985 Finke .................. B64D 15/163
    244/134 D
(Continued)

FOREIGN PATENT DOCUMENTS

| EP | 0701840 | 3/1996 |
|---|---|---|
| EP | 2756980 | 7/2014 |

(Continued)

OTHER PUBLICATIONS

European Patent Office, "Extended European Search Report from EP Application No. 17150722.1 dated May 22, 2017", "from Foreign Counterpart of U.S. Appl. 15/153,511", May 22, 2017, pp. 1-10.

(Continued)

*Primary Examiner* — Nathaniel C Chukwurah
*Assistant Examiner* — Lucas E. A. Palmer
(74) *Attorney, Agent, or Firm* — Bookoff McAndrews, PLLC

(57) ABSTRACT

Systems and methods for breaking a material are provided. In one embodiment, a system for breaking a material comprises a device configured to generate a force or torque on a material. The system further comprises at least one controller coupled to the device. The controller is configured to select at least one degree of freedom and an initial direction to apply the force or torque with the device. The controller is further configured to oscillate the force or torque at a first series of frequencies while applying the force or torque in the initial direction with the device by providing commands to the device.

13 Claims, 7 Drawing Sheets

(51) Int. Cl.
*A61C 1/07* (2006.01)
*A61B 17/22* (2006.01)
*A61C 3/03* (2006.01)
*A61C 1/00* (2006.01)

(52) U.S. Cl.
CPC ............ B25D 17/00 (2013.01); *A61C 1/0007* (2013.01); *A61C 3/03* (2013.01); *B25D 2222/15* (2013.01)

(58) Field of Classification Search
USPC .......................................................... 173/110
See application file for complete search history.

(56) References Cited

U.S. PATENT DOCUMENTS

| | | | |
|---|---|---|---|
| 4,629,149 A | 12/1986 | Carson et al. | |
| 5,004,964 A * | 4/1991 | Kataoka | H02N 2/14 310/51 |
| 5,010,350 A * | 4/1991 | Lipkin | H01Q 1/02 343/704 |
| 5,017,236 A * | 5/1991 | Moxness | B08B 3/12 134/1 |
| 5,025,187 A * | 6/1991 | Fujie | B60R 1/0602 15/250.001 |
| 5,066,070 A * | 11/1991 | Clarke | B25D 9/14 125/40 |
| 5,172,024 A * | 12/1992 | Broussoux | B06B 1/0688 310/321 |
| 5,191,791 A * | 3/1993 | Gerardi | B64D 15/16 73/178 R |
| 5,548,175 A * | 8/1996 | Tamai | H02N 2/0015 310/317 |
| 5,573,497 A | 11/1996 | Chapelon | |
| 5,696,421 A * | 12/1997 | Zumeris | H02N 2/103 310/323.02 |
| 5,905,351 A * | 5/1999 | Morishita | G05B 19/19 318/560 |
| 5,912,538 A | 6/1999 | Turner | |
| 6,100,654 A * | 8/2000 | Izukawa | H02N 2/142 310/317 |
| 6,917,326 B1 * | 7/2005 | Tregenza | B08B 7/02 342/118 |
| 7,084,553 B2 * | 8/2006 | Ludwiczak | B08B 7/02 310/321 |
| 7,211,927 B2 * | 5/2007 | Puskas | B01J 19/10 310/317 |
| 7,336,019 B1 * | 2/2008 | Puskas | A61L 2/02 310/317 |
| 7,960,925 B2 * | 6/2011 | Kudo | H02N 2/004 310/316.01 |
| 8,087,297 B2 * | 1/2012 | Ludwiczak | B06B 3/00 310/321 |
| 8,517,313 B2 | 8/2013 | Gornik | |
| 8,659,490 B2 | 2/2014 | Walton | |
| 9,048,760 B2 * | 6/2015 | Kataoka | H02N 2/142 |
| 9,507,331 B2 * | 11/2016 | Jones | G05B 15/02 |
| 2002/0043893 A1 * | 4/2002 | Puskas | B06B 1/0269 310/316.01 |
| 2005/0017599 A1 * | 1/2005 | Puskas | B01J 19/10 310/317 |
| 2006/0001330 A1 * | 1/2006 | Matsuzaki | H02N 2/004 310/316.01 |
| 2007/0090779 A1 * | 4/2007 | Atsuta | H02N 2/008 318/119 |
| 2008/0047575 A1 * | 2/2008 | Puskas | B08B 3/12 134/1 |
| 2008/0054762 A1 * | 3/2008 | Ludwiczak | B06B 3/00 310/323.01 |
| 2008/0143213 A1 * | 6/2008 | Kurosawa | H02N 2/142 310/316.02 |
| 2008/0275661 A1 * | 11/2008 | Yang | G03F 7/70725 702/105 |
| 2011/0005015 A1 * | 1/2011 | Iwahori | A61C 17/221 15/22.1 |
| 2011/0048475 A1 * | 3/2011 | Sinha | B08B 3/12 134/184 |
| 2011/0186077 A1 * | 8/2011 | Thompson | B08B 7/00 134/6 |
| 2011/0241786 A1 * | 10/2011 | Gilbert | A61B 17/320092 331/34 |
| 2011/0273344 A1 * | 11/2011 | Reams | H01Q 1/02 343/704 |
| 2012/0274520 A1 * | 11/2012 | Conti | H01Q 1/18 343/709 |
| 2013/0032671 A1 * | 2/2013 | Giles | B64D 15/16 244/134 R |
| 2013/0281897 A1 * | 10/2013 | Hoffmann | A61B 8/08 601/107 |
| 2014/0248581 A1 * | 9/2014 | Petersen | A61C 8/0089 433/119 |
| 2015/0133788 A1 * | 5/2015 | Mauldin, Jr. | A61B 8/0875 600/444 |
| 2015/0325904 A1 * | 11/2015 | Jones | G05B 15/02 343/704 |

FOREIGN PATENT DOCUMENTS

| | | |
|---|---|---|
| GB | 505433 | 5/1939 |
| WO | 2009019696 | 2/2009 |

OTHER PUBLICATIONS

European Patent Office, "Communication pursuant to Article 94(3) from EP Application No. 17150722.1 dated May 22, 2019", from Foreign Counterpart to U.S. Appl. No. 15/153,511, pp. 1-6, Published: EP.

* cited by examiner

ALGORITHM FOR EFFICIENTLY BREAKING A MATERIAL

PRIORITY CLAIM

The present application claims priority to, and the benefit of, U.S. Provisional Patent Application No. 62/281,157, entitled "ICE BREAKING ALGORITHM", which was filed on Jan. 20, 2016, the disclosure of which is incorporated herein by reference in its entirety.

BACKGROUND

Machines or tools are used to break, fracture, or otherwise change the state of materials by applying a force or torque to the material. During operation, it would be beneficial to apply force and/or torque at an optimal frequency to efficiently carry out the task. However, in most situations, the optimal frequency to break the material is not known for every situation and would be onerous or not possible to determine. For example, the optimal frequency to break concrete depends on the characteristics of the concrete, which may not be known ahead of time. Further, for most industrial and commercial applications, consistency in the machines or tools being sold results in a uniformity such that the machines or tools are not specifically tailored to breaking the particular material in all situations. For example, a jackhammer applies a force (e.g., drill bit impacting the ground) at a particular frequency that is fixed upon manufacture.

In the specific context of aviation, airborne terminals attached to an external surface of an aircraft encounter ice build-up conditions as the aircraft passes from cold dry conditions to warm humid conditions and vice versa. In particular, when aircraft move quickly from high altitudes having cold temperatures to lower altitudes with higher temperatures and humidity, icing conditions are experienced. In many situations, mechanical positioners included in the airborne terminals are not constantly moving and ice will accumulate, forming bridges or dams, on the gear surfaces or between stationary and moving mechanical parts. Teeth of gears are particularly susceptible to this phenomenon. Accumulated ice on terminals with moving parts may prevent the terminal from moving at times of initial startup and during nominal conditions.

Aircraft manufacturers seek to minimize the power consumption of the systems on the aircraft. Accordingly, there is usually a limited amount of current and thus torque available at all operating conditions to attempt to break any ice that builds up on the moving parts of the terminals. Attempts to seal the moving parts of the terminals from humidity are difficult to implement and increase the time and cost of producing the terminals. If the ice cannot be broken through, the positioning capability of the terminal is compromised to the point of mission failure.

For the reasons stated above and for other reasons stated below which will become apparent to those skill in the art upon reading and understanding the specification, there is a need in the art for improved systems and methods for efficiently breaking different materials.

SUMMARY

The embodiments of the present disclosure provide systems and methods for efficiently breaking different materials and will be understood by reading and studying the following specification.

In one embodiment, a system for breaking a material comprises a device configured to generate a force or torque on a material. The system further comprises at least one controller coupled to the device. The controller is configured to select at least one degree of freedom and an initial direction to apply the force or torque with the device. The controller is further configured to oscillate the force or torque at a first series of frequencies while applying the force or torque in the initial direction with the device by providing commands to the device.

DRAWINGS

Understanding that the drawings depict only exemplary embodiments and are not therefore to be considered limiting in scope, the exemplary embodiments will be described with additional specificity and detail through the use of the accompanying drawings, in which.

Figure 5A:
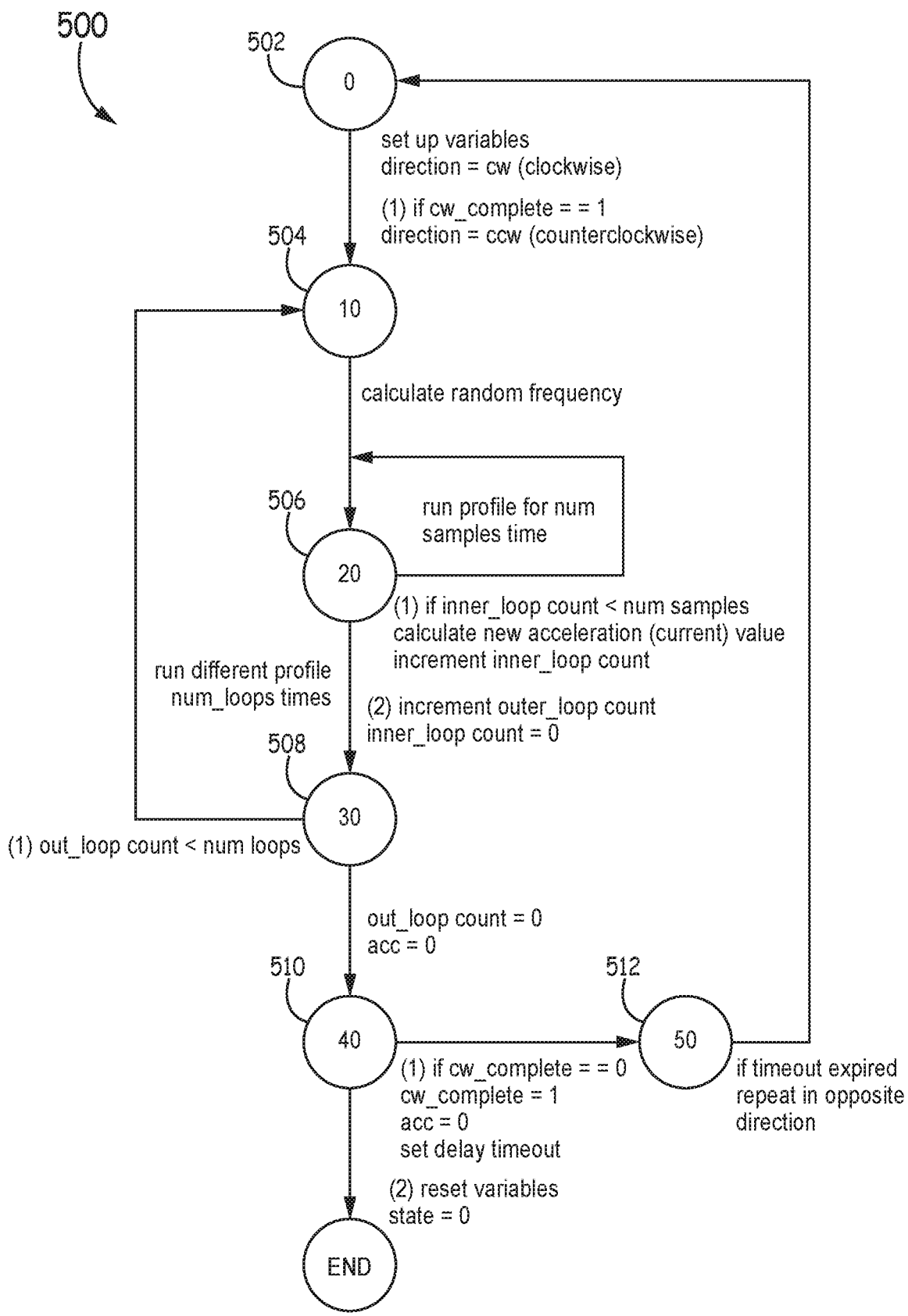
Figure 5B:
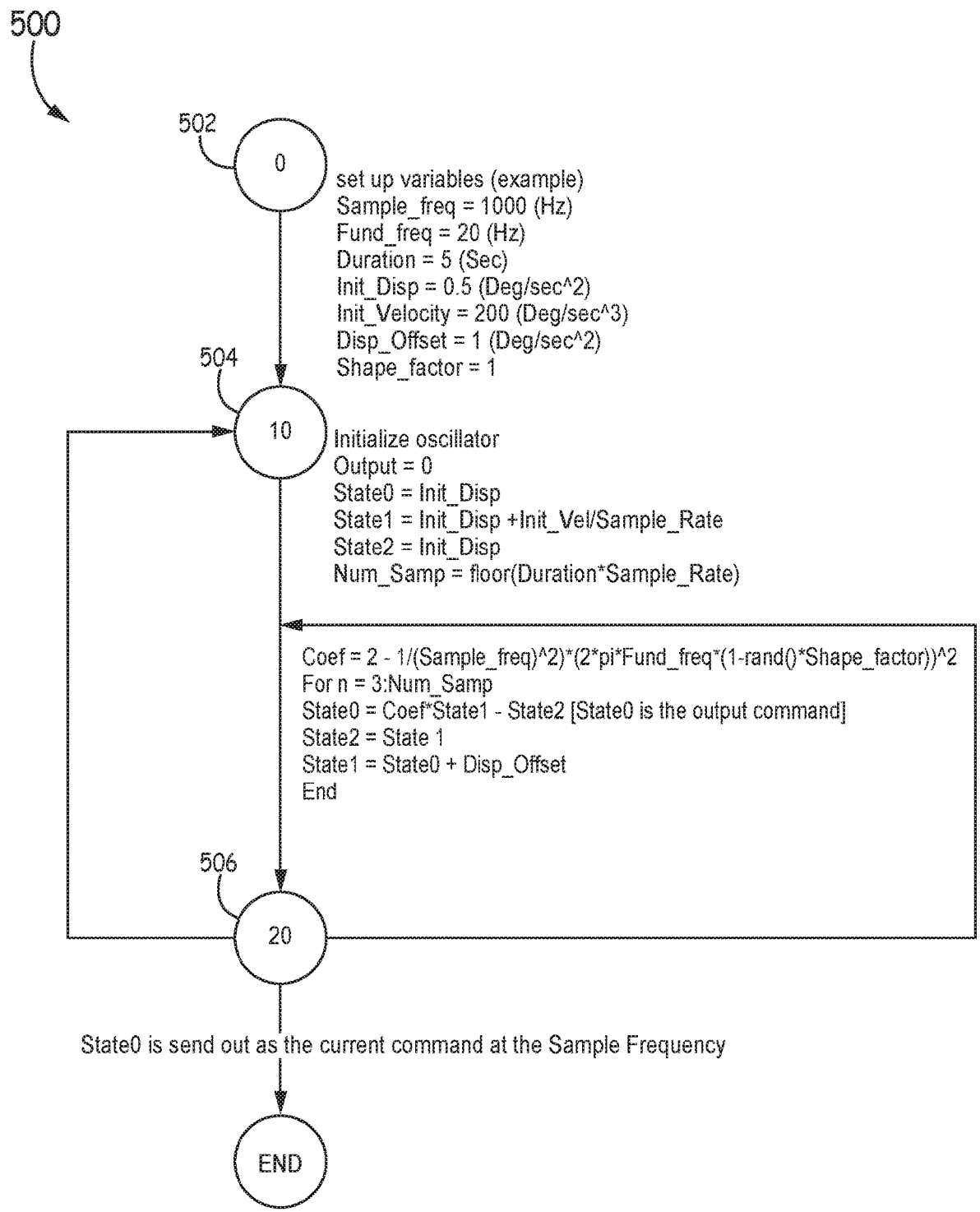

FIGS. 5A and 5B form a flow diagram of an example method of generating current commands for a positioner according to one embodiment of the present disclosure.

Figure 6:
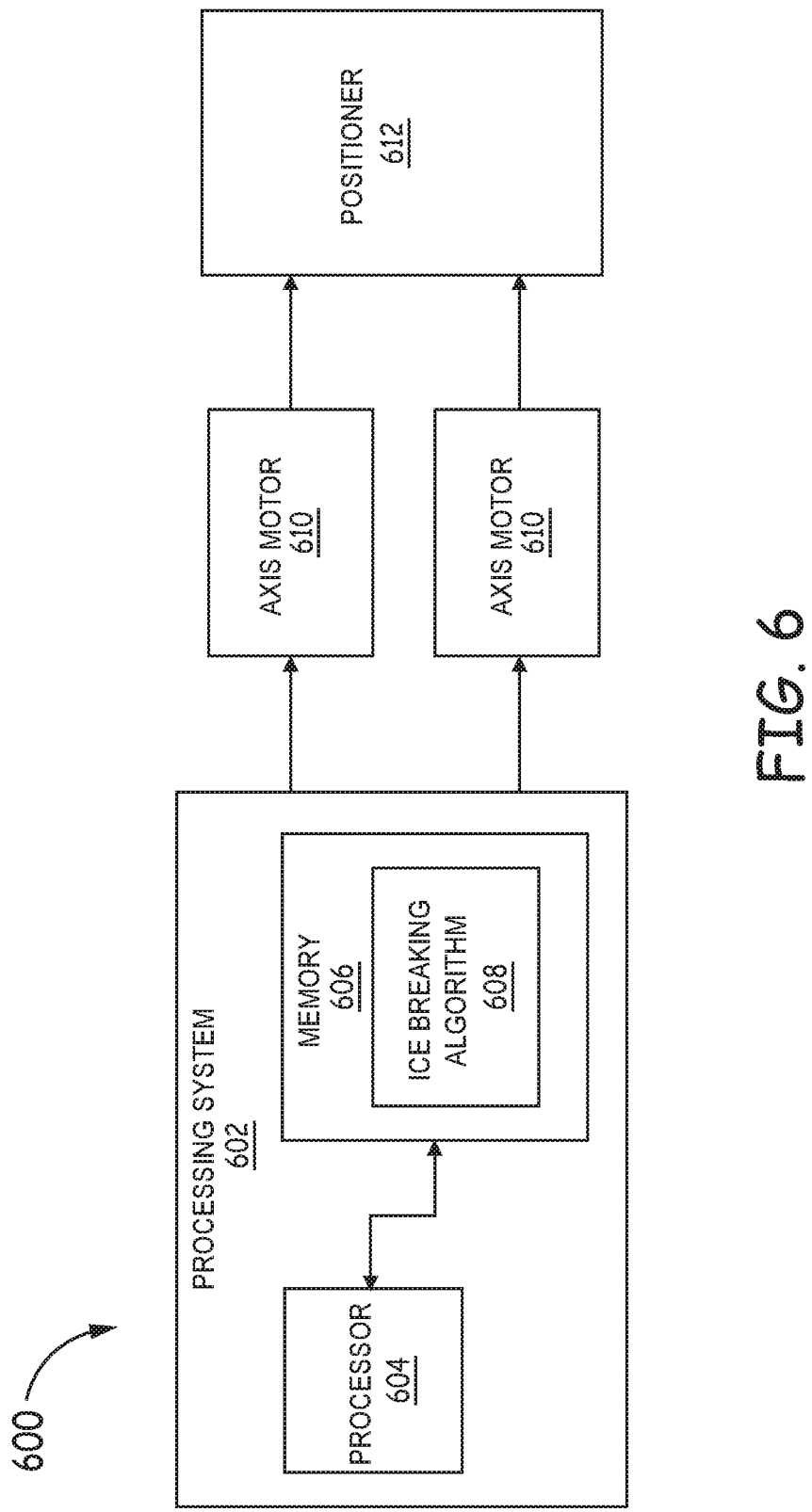

FIG. 6 is a block diagram of an example system that uses an ice breaking algorithm according to one embodiment of the present disclosure.

In accordance with common practice, the various described features are not drawn to scale but are drawn to emphasize specific features relevant to the exemplary embodiments.

DETAILED DESCRIPTION

In the following detailed description, reference is made to the accompanying drawings that form a part hereof, and in which is shown by way of illustration specific illustrative embodiments. However, it is to be understood that other embodiments may be utilized and that logical, mechanical, and electrical changes may be made. Furthermore, the method presented in the drawing figures and the specification is not to be construed as limiting the order in which the individual steps may be performed. The following detailed description is, therefore, not to be taken in a limiting sense.

Some machines are adjustable such that force or torque can be applied at multiple frequencies. However, such machines are not adjustable while applying the force or torque and the optimal frequency must still be determined prior to operation or through trial and error. The operator of such machines ceases operation of the machine to perform the frequency adjustment or determines the optimal frequency prior to operation, which leads to inefficiencies.

In the particular application of breaking ice, previous methods of ice breaking for mechanical positioners included using constant (DC) current commands to alternately move the positioner in both directions (e.g., clockwise and counterclockwise) with the maximum amount of current available. These methods were not successful in consistently breaking ice build-up on mechanical positioners for aircraft terminals.

Embodiments of the present disclosure provide systems and methods for efficiently breaking a material. In particular, the embodiments oscillate a force or torque at a series of frequencies while applying the force or torque in the initial direction. Oscillating the force or torque at a series of frequencies during application of the force or torque enables more efficient breaking of a material. In particular, by applying the force or torque at multiple different frequencies, the chances of applying the force or torque at the optimal frequency increases and removes the necessity of determining the optimal frequency prior to operation. Further, since the frequency of the force or torque can be changed while applying the force or torque, ceasing the application of the force or torque to adjust the frequency is not required using the embodiments of the present disclosure.

Figure 1:
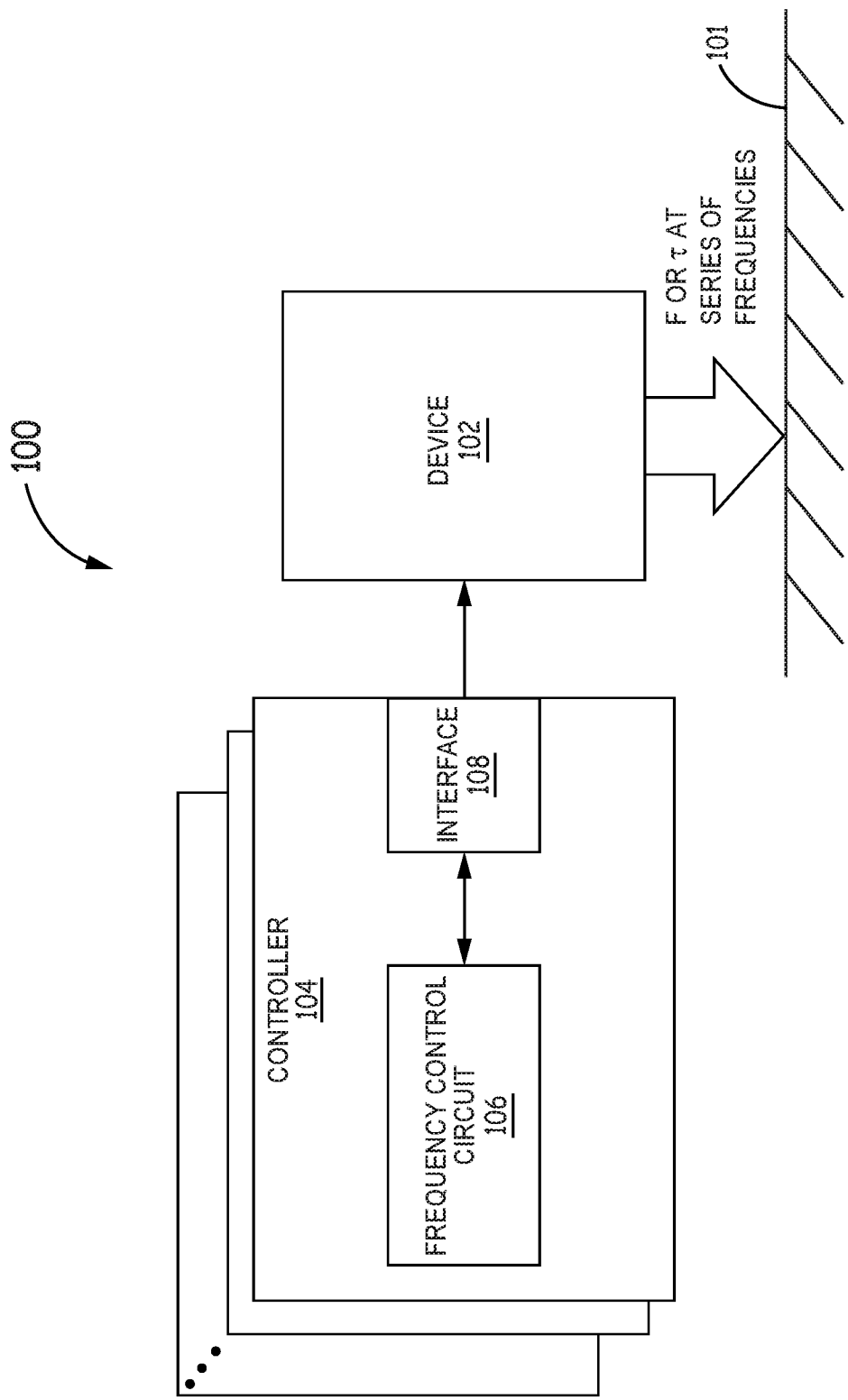
FIG. 1 is a block diagram of an example system for breaking a material according to one embodiment of the present disclosure.

FIG. 1 is a block diagram of one exemplary embodiment of a system 100 that uses an algorithm for efficiently breaking a material 101. System 100 includes a device 102 coupled to a controller 104. In exemplary embodiments, the system 100 includes a plurality of controllers 104 where each respective controller 104 controls a respective degree of freedom of the device 102.

The device 102 is configured to provide a force or torque on a material 101 to be broken. In exemplary embodiments, the device 102 can comprise any machine or tool used to break a material. As the term is used herein, to "break" a material means to break, fracture, or otherwise change the state of a material. In one embodiment, the device 102 is a jackhammer, which can be used to break asphalt, concrete, rocks, or the like. In another embodiment, the device 102 is an ultrasonic wave generator, which can be used to break eye lenses (cataract surgery), kidney stones, blot clots, scar tissue, fat globules (milk processing), or the like. In another embodiment, the device 102 is a dentistry tool, which can be used to break up teeth. In another embodiment, the device 102 is a hydraulic breaker, which can be used to break concrete, rocks, or the like. In another embodiment, the device 102 is a pneumatic breaker, which can be used to break concrete, rocks, or the like. In another embodiment, the device 102 is a crusher, which can be used to break down rocks, waste, or other materials. In another embodiment, the device 102 can comprise a positioner, which can be used to break ice or other materials built up on the components of the positioner. For example, the positioner may be an antenna positioner.

In exemplary embodiments, the controller includes a frequency control circuit 106 and an interface 108. The characteristics of the controller 104, including the frequency control circuit 106 and the interface 108, depend on the particular device 102 that it controls. In exemplary embodiments, the controller 104 may comprise a mechanical controller, an electrical controller, a hydraulic controller, a pneumatic controller, or another type of controller for a machine known to one having skill in the art.

The controller 104 is configured to control or regulate the operation of the device 102 by providing commands to the device 102 via the interface 108. The interface 108 may comprise any appropriate communication interface between the controller 104 and the device 102. In exemplary embodiments, the controller 104 is configured to select at least one degree of freedom and an initial direction to apply a force or torque with the device 102. The controller 104 is also configured to oscillate the force or torque at a series of frequencies while applying the force or torque in the initial direction by providing commands to the device 102. The frequency control circuit 106 generates the commands that oscillate the force or torque at a series of frequencies. In some embodiments, the frequency control circuit 106 is configured to generate the commands that oscillate the force or torque at the series of frequencies using a random number generator. In exemplary embodiments, the frequency control circuit 106 may comprise a processor coupled to a memory, where the processor is configured to generate the commands described above by executing appropriate instructions stored in the memory.

Figure 2:
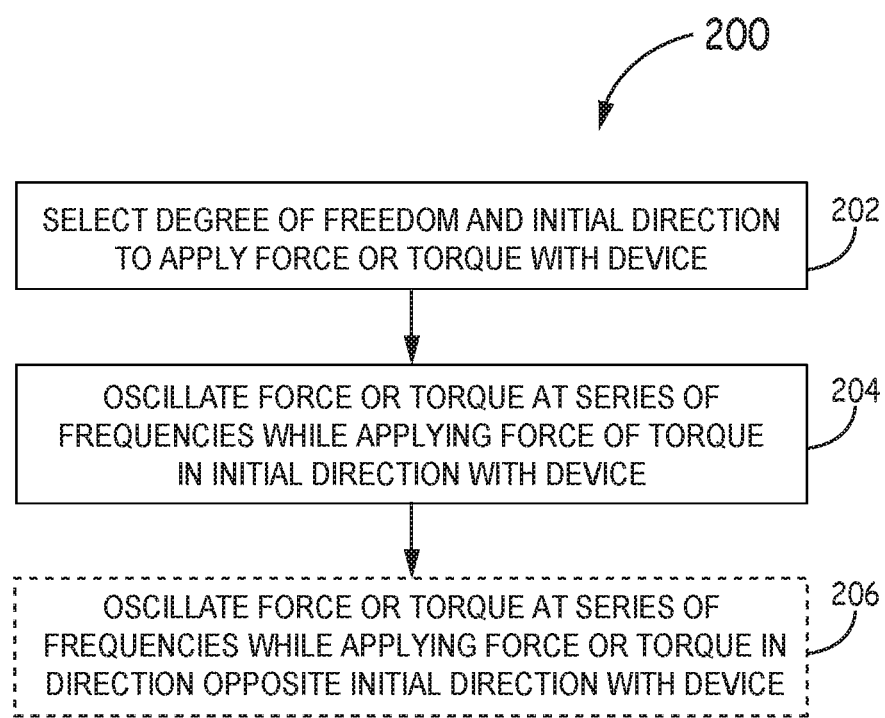
FIG. 2 is a flow diagram of an example method of breaking a material according to one embodiment of the present disclosure.

FIG. 2 is an example method 200 of operating a device according to one embodiment of the present disclosure. The functions, structures, and other description of elements for such embodiments described herein may apply to like named elements of method 200 and vice versa. In exemplary embodiments, method 200 is performed by a controller (such as, for example, controller 104) of a device (such as, for example, device 102).

The method begins with selecting at least one degree of freedom and an initial direction to apply a force or torque with the device (block 202). In the example of an antenna positioner, the initial direction could be clockwise or counterclockwise. For other types of devices, the directions may be referred to with different nomenclature known to one having skill in the art.

The method proceeds with oscillating the force or torque at a series of frequencies while applying the force or torque in the initial direction with the device (block 204). In exemplary embodiments, the series of frequencies are generated using a random number generator that uses designated variables. The variables can be preset in the system or can be manually entered upon initiation of the method 200. In the example of an antenna positioner, the variables can include, but are not limited to, the initial velocity of the positioner, the fundamental frequency of oscillating the positioner, and the duration of applying each random frequencies.

In exemplary embodiments, the method optionally proceeds with oscillating the force or torque at a different series of frequencies while applying the force or torque in a direction opposite the initial direction with the device (block 206). In some embodiments (for example, a jackhammer), the force or torque need only be applied in the initial direction to sufficiently break the material. In other embodiments (for example, an antenna positioner), the force or torque may need to be applied in multiple directions to sufficiently break the material.

Figure 3:
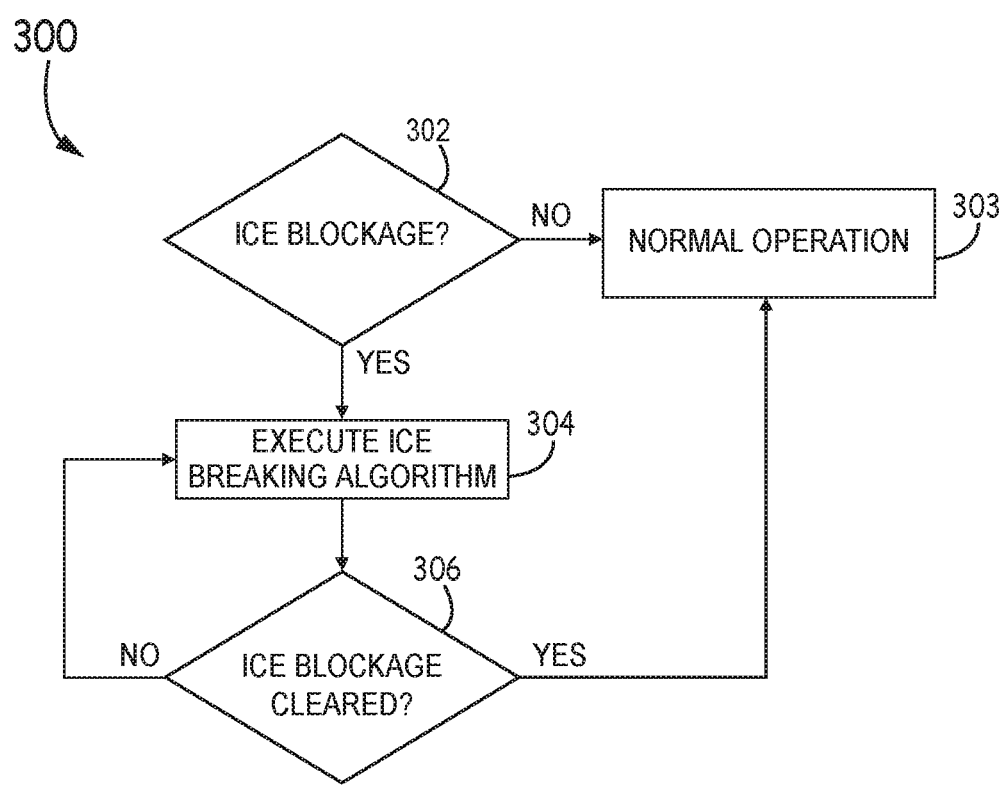
FIG. 3 is a flow diagram of an example method of operating a positioner according to one embodiment of the present disclosure.

FIG. 3 is an example method of operating a positioner according to one embodiment of the present disclosure. The functions, structures, and other description of elements for such embodiments described herein may apply to like named elements of method 300 and vice versa. While the description of method 300 is with respect to a mechanical positioner, it should be understood to one having skill in the art that the method 300 is applicable to other types of positioners as well.

The method begins with determining whether the mechanical positioner has an ice blockage (block 302). This includes testing the range of motion of the mechanical positioner for all axes. In some embodiments, both directions of each axis are tested. In exemplary embodiments, the mechanical positioner is a satellite communications (SATCOM) antenna positioner having both azimuth and elevation axes. In such embodiments, the testing would include moving the mechanical positioner through the full specified range of the elevation axis and azimuth axis. The elevation axis for a SATCOM antenna positioner typically has a specified range of approximately 92 degrees. The azimuth axis for a SATCOM antenna positioner typically has a specified range of 360 degrees. As discussed above, the testing can include moving the positioner in both directions through the full range of each axis.

The velocity of rotation of the positioner during the testing and the distance of the full range of the positioner for a particular axis is known prior to operation. Thus, a system operating the positioner can calculate the amount of time it should take the positioner to travel the full range of an axis with precision. Accordingly, if the system detects that the positioner completes the full range of motion within a threshold time (for example, the calculated time plus an acceptable delay), then an ice blockage is not present. If the positioner fails to complete the full range of motion within the threshold time, then an ice blockage is present.

When it is determined that the mechanical positioner does not have any ice blockages for all of its axes in both directions, the method proceeds with normal operation of the mechanical positioner (block 303). When it is determined that the mechanical positioner has an ice blockage, the method proceeds with executing an ice breaking algorithm (block 304), which is discussed herein with respect to FIGS. 4, 5A and 5B.

After completing the ice breaking algorithm, the method proceeds with determining whether the ice blockage has been cleared (block 306). In exemplary embodiments, this determination includes similar testing steps discussed above with respect to the initial determination (block 302). When it is determined that mechanical positioner no longer has an ice blockage, the method proceeds with normal operation of the mechanical positioner (block 303). When it is determined that a mechanical positioner still has an ice blockage, then the method proceeds with executing the ice breaking algorithm again (block 304).

Figure 4:
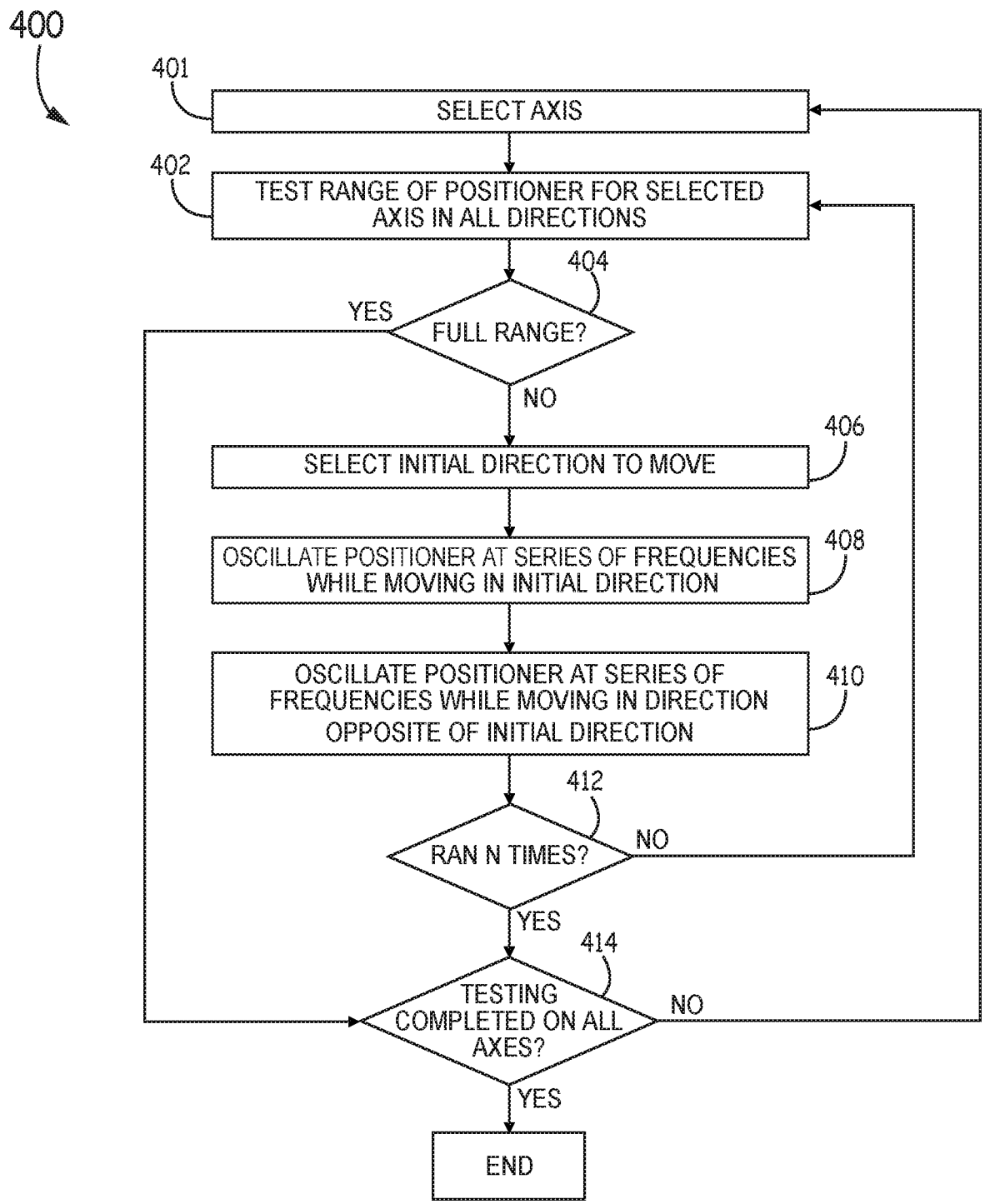
FIG. 4 is a flow diagram of an example method of breaking ice on a positioner according to one embodiment of the present disclosure.

FIG. 4 is a flow diagram of an example method 400 of ice breaking on a positioner according to one embodiment of the present disclosure. The functions, structures, and other description of elements for such embodiments described herein may apply to like named elements of method 400 and vice versa. While the description of method 400 is with respect to a mechanical positioner, it should be understood to one having skill in the art that the method 400 is applicable to other types of positioners as well.

The method begins with selecting an axis (block 401). In the example of a SATCOM mechanical positioner, the elevation or azimuth axis can be selected. For other types of positioners, the axes may be referred to with different nomenclature known to one having skill in the art. While the description of method 400 is with respect to axes, it should be understood to one having skill in the art that the method 400 is applicable to other degrees of freedom beyond axes.

The method proceeds with testing the range of motion of the mechanical positioner for the selected axis (block 402). In exemplary embodiments, the testing is similar to that described above with respect to block 106. The method then proceeds to determining whether the selected axis has a full range of operation (block 404). If the mechanical positioner does not have an ice blockage for the test axis (e.g., the mechanical position has a full range of motion in the tested direction), then the method proceeds with determining whether testing has been completed for all axes (block 414).

If the mechanical positioner has an ice blockage for the test axis (e.g., the mechanical position does not have a full range of motion in the tested direction), then the method proceeds with selecting an initial direction to move the positioner (block 406). In the example of a SATCOM mechanical positioner, the initial direction could be clockwise or counterclockwise. For other types of positioners, the directions may be referred to with different nomenclature known to one having skill in the art.

The method proceeds with oscillating the positioner at a series of frequencies while moving the positioner in the initial direction (block 408). In exemplary embodiments, the series of frequencies are generated using a random number generator that uses designated variables. The variables can be preset in the system or can be manually entered upon initiation of the method 400. In exemplary embodiments, the variables can include, but are not limited to, the initial velocity of the positioner, the fundamental frequency of oscillating the positioner, and the duration of applying each random frequencies.

The positioner is oscillated at a particular frequency for a selected amount of time. For example, the positioner is oscillated at each frequency for approximately ten seconds. It should be understood that any appropriate length of time could be used. After the selected amount of time expires, the frequency of oscillation is changed to another frequency. In some embodiments, the random number generator is used to generate each frequency. In other embodiments, the first frequency is generated using the random number generator, but the frequencies after are set to sweep a particular range of frequencies. The frequencies may be set to sweep by increasing or decreasing the frequency by a selected amount (for example, 10 Hz). The frequency in either the random frequency or the sweeping frequency embodiments can be limited to a particular range to ensure that there is a sufficient amount of torque generated by the positioner to break the ice.

In some embodiments, the movement of the positioner in the initial direction is restricted to a certain period of time. For example, the movement of the positioner in the first direction can be limited to 100 seconds, which could include oscillating the positioner with ten different frequencies for ten seconds each. In other embodiments, the movement of the positioner in the initial direction is not restricted to a period of time and continues until the positioner reaches the end of the range of the axis in the initial direction.

Once the positioner motion in the initial direction stops (either after the time period or upon reaching the end of the range), the method proceeds with oscillating the positioner at a series of frequencies while moving the positioner in the direction opposite of the initial direction (block 410). In exemplary embodiments, oscillating the positioner while moving the positioner in the direction opposite of the initial direction can operate similarly to the description above with respect to block 408.

Once the positioner reaches the end of the range of the axis in the direction opposite of the initial direction or has reached the time limit, the method proceeds with determining whether the process described above with respect to blocks 402-410 has been run a selected number ("N") of times (block 412). For example, the selected number may be six or any other appropriate number. Ideally, the selected number will be large enough to virtually guarantee that an ice blockage will be broken. If the method has not been run the selected number of times, then the method proceeds with testing the range of motion of the mechanical positioner for the selected axis (block 402) as described above.

If the process has been run the selected number of times, then the method proceeds with determining whether testing has been completed for all axes (block 414). When testing has not been completed for all axes, the method proceeds with selecting a different test axis (block 401). In the example of a SATCOM positioner having both elevation and azimuth axes, the method 400 could first be used to clear the ice blockage for the elevation axis and then be used to clear the ice blockage for the azimuth axis. When testing has been completed for all axes, the method 400 ends.

FIGS. 5A-5B illustrate a flow diagram of an example method 500 of generating commands for a positioner according to one embodiment of the present disclosure. In particular, FIGS. 5A-5B illustrate a specific implementation for an antenna positioner, but could be utilized for other positioners with similar characteristics. The functions, structures, and other description of elements for such embodiments described herein may apply to like named elements of method 500 and vice versa. While the description of method 500 is with respect to a mechanical positioner and current commands, it should be understood to one having skill in the art that the method 500 is applicable to other types of positioners and commands as well.

The method begins with entering set up variables, setting the initial direction of motion to clockwise, and initializing the oscillator (block 502). In the example of FIG. 5B, the set up variables include a sample frequency (sample_freq), a fundamental frequency (fund_freq), a duration of time that a particular frequency current command will be applied (duration), an initial displacement of the positioner (init_disp), an initial velocity of the positioner (init_velocity or init_vel), a displacement offset (disp_offset), and a shape factor (shape_factor). Example values for each of these variables are included in FIG. 5B. It should be understood that these variables and the values of these variables are for illustration purposes and that different variables and values for these variables could also be used if desired. As shown in FIG. 5B, initializing the oscillator includes setting up initial states and determining the amount of samples used.

The method proceeds with generating a random frequency (block 504). In the example of FIGS. 5A-5B, this includes calculating a frequency using a random number generator. This is shown as "Coef" in FIG. 5B using the variables, a random number generator, and the following equation:

$$Coef = 2 - \frac{1}{sample\_freq^2} \times (2\pi \times fund\_freq \times (1 - rand() \times shape\_factor))^2$$

In exemplary embodiments, the random number is generated between the values of 0 and 1. Following the generation of the random frequency using the equation above, the states of the oscillator are updated and the current command is sent with the random frequency. As shown in FIG. 5A, the current command is sent for a selected number of samples (block 506), which corresponds to the duration variable discussed above. In the specific implementation shown in FIG. 5A, the method 500 repeats the process described above with respect to blocks 504-506 to complete a selected number of loops (num_loops).

After completing the selected number of samples for one frequency, the method proceeds with determining whether a selected number of loops (num_loops) have been completed (block 508). The selected number of loops correspond to a particular number of random frequencies that are to be used. When the selected number of loops have not been completed, the method proceeds with repeating the process described above with respect to blocks 504-506. When the selected number of loops have been completed, the method proceeds with setting a status of the clockwise direction to complete, setting the acceleration to zero, and setting a delay timeout (block 510). When the timeout expires, the process described above with respect to blocks 502-508 is repeated for the counterclockwise direction. After completing the counterclockwise direction, the method 500 ends.

FIG. 6 is a block diagram of one exemplary embodiment of a system 600 that uses an ice breaking algorithm. System 600 includes a processing unit 602 and at least one axis motor 610 coupled to a positioner 612. In exemplary embodiments, the system 600 includes a plurality of axis motors 610 where each respective axis motor 610 controls a respective degree of freedom of the positioner 612.

The processing unit 602 includes at least one processor 604 coupled to a memory 606. The memory 606 includes the ice breaking algorithm 608, which may comprise computer readable instructions for executing any of the methods described above with respect to FIGS. 3, 4, 5A and 5B. The processing unit 602 communicates current (torque) commands to the axis motor 610 during execution of the ice breaking algorithm 608. The axis motors 610 transfer torque to the gears of the positioner 612 at the particular frequency that corresponds to the current commands output from the processing unit 602.

Example Embodiments

Example 1 includes a system for breaking a material, comprising: a device configured to generate a force or torque on a material; and at least one controller coupled to the device, wherein the controller is configured to: select at least one degree of freedom and an initial direction to apply the force or torque with the device; and oscillate the force or torque at a first series of frequencies while applying the force or torque in the initial direction with the device by providing commands to the device.

Example 2 includes the system of Example 1, wherein the device includes one of: a jackhammer; an ultrasonic wave generator; a dentistry tool; a hydraulic breaker; a pneumatic breaker; a crusher; or a positioner.

Example 3 includes the system of Example 2, wherein the at least one controller includes at least one of: a mechanical controller; an electrical controller; a hydraulic controller; and a pneumatic controller.

Example 4 includes the system of any of Examples 1-2, wherein one or more frequencies of the first series of frequencies are generated using a random number generator.

Example 5 includes the system of any of Examples 1-4, wherein an initial frequency of the first series of frequencies is generated using a random number generator, wherein remaining frequencies of the first series of frequencies are generated by sweeping selected a range of frequencies.

Example 6 includes a method of breaking a material, comprising: selecting at least one degree of freedom and initial direction to apply a force or a torque to a material with a device; and oscillating the force or torque at a first series of frequencies while applying the force or torque in the initial direction with the device by providing commands from a controller to the device.

Example 7 includes the method of Example 6, further comprising oscillating the force or torque at a second series of frequencies while applying the force or torque in a direction opposite the initial direction with the device by providing commands from the controller to the device.

Example 8 includes a system comprising: a positioner; at least one prime mover coupled to the positioner; and at least one controller coupled to the at least one prime mover, wherein the controller is configured to: select a degree of freedom and initial direction to move the positioner; oscillate the positioner at a first series of frequencies while moving the positioner in the initial direction by providing commands to the at least one prime mover; oscillate the positioner at a second series of frequencies while moving the positioner in a direction opposite the initial direction by providing commands to the at least one prime mover; and test a range of motion of the positioner for the degree of freedom in both the initial direction and the direction opposite the initial direction.

Example 9 includes the system of Example 8, wherein the positioner comprises an antenna positioner.

Example 10 includes the system of Example 9, wherein the at least one prime mover comprises one or more axis motors mechanically coupled to the antenna positioner.

Example 11 includes the system of Example 10, wherein the at least one controller comprises a processor coupled to a memory, wherein the processor is communicatively coupled to the one or more axis motors, wherein the commands provided to the one or more axis motors comprise current commands.

Example 12 includes the system of Example 11, wherein the entire first series of frequencies and the entire second series of frequencies are generated using a random number generator.

Example 13 includes the system of Example 11, wherein an initial frequency of the first series of frequencies is generated using a random number generator, wherein remaining frequencies of the first series of frequencies are generated by sweeping a selected range of frequencies.

Example 14 includes the system of any of Examples 8-13, wherein the at least one controller is configured to oscillate the positioner at a first series of frequencies while moving the positioner in the initial direction until the positioner reaches the end of the range of motion of the positioner for the degree of freedom in the initial direction.

Example 15 includes the system of Example 8, wherein the controller is configured to oscillate the positioner at a first series of frequencies while moving the positioner in the initial direction for a selected period of time.

Example 16 includes a method of breaking ice from a positioner, comprising: selecting a degree of freedom and initial direction to move the positioner; oscillating the positioner at a first series of frequencies while moving the positioner in the initial direction; oscillating the positioner at a second series of frequencies while moving the positioner in a direction opposite the initial direction; and testing a range of motion of the positioner for the degree of freedom in both the initial direction and the direction opposite the initial direction.

Example 17 includes the method of Example 16, wherein the first series of frequencies and the second series of frequencies are generated using a random number generator.

Example 18 includes the method of Example 16, wherein an initial frequency of the first series of frequencies is generated using a random number generator, wherein remaining frequencies of the first series of frequencies are generated by sweeping a selected range of frequencies.

Example 19 includes the method of any of Examples 16-18, wherein testing a range of motion of the positioner includes determining whether the positioner completes a full range of motion within a threshold time.

Example 20 includes the method of Example 19, when the positioner does not complete the full range of motion within the threshold time, further comprising: oscillating the positioner at a third series of frequencies while moving the positioner in the initial direction; oscillating the positioner at a fourth series of frequencies while moving the positioner in the direction opposite the initial direction; and testing the range of motion of the positioner for the degree of freedom in both the initial direction and the direction opposite the initial direction.

The processor 604 and some embodiments of the controller 104 include or functions with software programs, firmware or other computer readable instructions for carrying out various methods, process tasks, calculations, and control functions.

These instructions are typically stored on any appropriate computer readable medium used for storage of computer readable instructions or data structures. The computer readable medium can be implemented as any available media that can be accessed by a general purpose or special purpose computer or processor, or any programmable logic device. Suitable processor-readable media may include storage or memory media such as magnetic or optical media. For example, storage or memory media may include conventional hard disks, Compact Disk-Read Only Memory (CD-ROM), volatile or non-volatile media such as Random Access Memory (RAM) (including, but not limited to, Synchronous Dynamic Random Access Memory (SDRAM), Double Data Rate (DDR) RAM, RAMBUS Dynamic RAM (RDRAM), Static RAM (SRAM), etc.), Read Only Memory (ROM), Electrically Erasable Programmable ROM (EEPROM), and flash memory, etc. Suitable processor-readable media may also include transmission media such as electrical, electromagnetic, or digital signals, conveyed via a communication medium such as a network and/or a wireless link.

Although specific embodiments have been illustrated and described herein, it will be appreciated by those of ordinary skill in the art that any arrangement, which is calculated to achieve the same purpose, may be substituted for the specific embodiments shown. Therefore, it is manifestly intended that this invention be limited only by the claims and the equivalents thereof.

What is claimed is:

1. A system for breaking a material, comprising:
    a device configured to apply a force or torque to a material to be broken; and
    at least one controller coupled to the device, wherein the at least one controller is configured to:
        select at least one degree of freedom of the device and an initial direction to apply the force or torque with the device; and
        apply the force or torque in the initial direction with the device by providing commands to the device, wherein the force or torque is varied at a first series of frequencies while the force or torque is continuously applied to the material to be broken in the initial direction.

2. The system of claim 1, wherein the device includes one of: a jackhammer; an ultrasonic wave generator; a dentistry tool; a hydraulic breaker; a pneumatic breaker; a crusher; or a positioner.

3. The system of claim 2, wherein the at least one controller includes at least one of: a mechanical controller; an electrical controller; a hydraulic controller; and a pneumatic controller.

4. The system of claim 1, wherein one or more frequencies of the first series of frequencies are generated using a random number generator.

5. The system of claim 1, wherein an initial frequency of the first series of frequencies is generated using a random number generator, wherein remaining frequencies of the first series of frequencies are generated by sweeping a selected range of frequencies.

6. A system comprising:
a positioner;
at least one prime mover coupled to the positioner; and
at least one controller coupled to the at least one prime mover, wherein the at least one controller is configured to:
 select a degree of freedom and initial direction to move the positioner;
 oscillate the positioner at a first series of frequencies while moving the positioner in the initial direction by providing commands to the at least one prime mover;
 oscillate the positioner at a second series of frequencies while moving the positioner in a direction opposite the initial direction by providing commands to the at least one prime mover; and
 test a range of motion of the positioner for the degree of freedom in both the initial direction and the direction opposite the initial direction.

7. The system of claim 6, wherein the positioner comprises an antenna positioner, wherein the antenna positioner comprises an azimuth axis and elevation axis.

8. The system of claim 7, wherein the at least one prime mover comprises an azimuth axis motor mechanically coupled to the antenna positioner and an elevation axis motor mechanically coupled to the antenna positioner.

9. The system of claim 8, wherein the at least one controller comprises a processor coupled to a memory, wherein the processor is communicatively coupled to the azimuth axis motor and the elevation axis motor, wherein the commands provided to the azimuth axis motor and the elevation axis motor comprise current commands.

10. The system of claim 9, wherein the entire first series of frequencies and the entire second series of frequencies are generated using a random number generator.

11. The system of claim 9, wherein an initial frequency of the first series of frequencies is generated using a random number generator, wherein remaining frequencies of the first series of frequencies are generated by sweeping a selected range of frequencies.

12. The system of claim 6, wherein the at least one controller is configured to oscillate the positioner at a first series of frequencies while moving the positioner in the initial direction until the positioner reaches the end of the range of motion of the positioner for the degree of freedom in the initial direction.

13. The system of claim 6, wherein the at least one controller is configured to oscillate the positioner at a first series of frequencies while moving the positioner in the initial direction for a selected period of time.

* * * * *